(12) United States Patent
McKenna

(10) Patent No.: US 10,695,585 B2
(45) Date of Patent: Jun. 30, 2020

(54) SPHERICAL RADIOTHERAPY PHANTOM

(71) Applicant: John T. McKenna, New York, NY (US)

(72) Inventor: John T. McKenna, New York, NY (US)

(*) Notice: Subject to any disclaimer, the term of this patent is extended or adjusted under 35 U.S.C. 154(b) by 54 days.

(21) Appl. No.: 16/059,466

(22) Filed: Aug. 9, 2018

(65) Prior Publication Data

US 2019/0060673 A1 Feb. 28, 2019

Related U.S. Application Data

(60) Provisional application No. 62/542,832, filed on Aug. 9, 2017.

(51) Int. Cl.
| | | |
|---|---|---|
| *A61N 5/10* | (2006.01) |
| *G01T 1/02* | (2006.01) |
| *G01T 7/00* | (2006.01) |
| *G01T 1/169* | (2006.01) |
| *G01T 1/29* | (2006.01) |

(52) U.S. Cl.
CPC .............. *A61N 5/1075* (2013.01); *G01T 1/02* (2013.01); *G01T 1/169* (2013.01); *G01T 1/29* (2013.01); *G01T 7/00* (2013.01); *A61N 2005/1076* (2013.01)

(58) Field of Classification Search
CPC .......... A61N 5/1075; A61N 2005/1076; G01T 1/02; G01T 1/169; G01T 1/29; G01T 7/00
USPC ........................................................ 378/207
See application file for complete search history.

(56) References Cited

U.S. PATENT DOCUMENTS

| | | | |
|---|---|---|---|
| 6,712,508 B2 | 3/2004 | Nilsson et al. | |
| 6,904,162 B2 | 6/2005 | Robar et al. | |
| 8,039,790 B2 | 10/2011 | Cho et al. | |
| 8,921,766 B2 | 12/2014 | Schiefer | |
| 2003/0004503 A1* | 1/2003 | Nilsson | A61B 6/583 606/11 |
| 2004/0120560 A1* | 6/2004 | Robar | A61N 5/1048 382/128 |

(Continued)

FOREIGN PATENT DOCUMENTS

| | | |
|---|---|---|
| EP | 1468709 A1 | 10/2004 |
| WO | 03/105956 A1 | 12/2003 |

OTHER PUBLICATIONS

Title: Lucy 3D QA Phantom, Publisher: Standard Imaging, Inc. (Year: 2010).*

(Continued)

*Primary Examiner* — Taeho Jo
(74) *Attorney, Agent, or Firm* — FisherBroyles, LLP; Robert Kinberg

(57) ABSTRACT

A spherical radiotherapy phantom for use with a source of radiation to receive a radiation dose distribution along a selected plane includes a spherical body comprising two hemispheres detachably connected together and comprising a solid homogenous material including a hollow compartment with a defined volumetric shape. A cartridge comprising a number of parallel planar plates, each configured to accommodate a planar radiation detecting medium and fitting together to form a shape corresponding to the defined volumetric shape of the hollow compartment, fits form fittingly in the hollow compartment when the two hemispheres are connected together.

22 Claims, 7 Drawing Sheets

(56) References Cited

U.S. PATENT DOCUMENTS

| | | | | |
|---|---|---|---|---|
| 2005/0139758 A1* | 6/2005 | White | ............... | A61B 6/583 |
| | | | | 250/252.1 |
| 2010/0288916 A1* | 11/2010 | Cho | ............... | G01D 15/00 |
| | | | | 250/252.1 |
| 2012/0305793 A1* | 12/2012 | Schiefer | ............... | A61N 5/1075 |
| | | | | 250/394 |
| 2018/0339173 A1* | 11/2018 | Kilby | ............... | A61N 5/1075 |

OTHER PUBLICATIONS

M. P. Grams and L. E. F. de los Santos, "Design and clinical use of a rotational phantom for dosimetric verification of IMRT/VMAT treatments," Physica Medica, vol. 50, pp. 59-65, 2018.

C. Constantinou, F. H. Attix and B. R. Paliwal, "A solid water phantom material for radiotherapy x-ray and γ-ray beam calibrations," Med. Phys., vol. 9, No. 3, pp. 436-441, 1982.

Standard Imaging, Inc. "Lucy 3D QA Phantom Brochure" 2017 https://www.standardimaging.com/uploads/files/Lucy_BR_1294-25.pdf.

Mack et al. "Quality assurance in stereotactic space. A system test for verifying the accuracy of aim in radiosurgery" Medical Physics, Apr. 2002, vol. 29, No. 4, pp. 561-568.

Drzymala et al. "Calibration of the Gamma Knife using a new phantom following the AAPM TG51 and TG21 protocols" Medical Physics, Feb. 2008, vol. 35, No. 2, pp. 514-521.

Novotny, Jr. et al. "Assessment of variation in Elekta® plastic spherical-calibration phantom and its impact on the Leksell Gamma Knife® calibration" Medical Physics, Sep. 2010, vol. 37, No. 9, pp. 5066-5071.

Sarkar et al. "Head to head comparison of two commercial phantoms used for SRS QA" Journal of Radiosurgery and SBRT, 2016, vol. 4, pp. 213-223.

Chung et al. "Development of a PMMA phantom as a practical alternative for quality control of gamma knife® dosimetry" Radiation Oncology, 2018 13:176, 9 Pages.

Mack et al. "Analyzing 3-tesla magnetic resonance imaging units for implementation in radiosurgery" J. Neurosurg., Jan. 2005, vol. 102, pp. 158-164.

D. R. White, R. J. Martin and R. Darlison, "Epoxy resin based tissue substitutes," British Journal of Radiology, Nov. 1977, vol. 50, No. 599, pp. 814-821.

* cited by examiner

SPHERICAL RADIOTHERAPY PHANTOM

CROSS-REFERENCE TO RELATED APPLICATIONS

This application claims priority to U.S. Provisional Application No. 62/542,832, filed Aug. 9, 2017, the entire content of which is incorporated herein by reference.

BACKGROUND

The present invention relates to the field of radiation therapy. Radiation therapy is the therapeutic use of ionizing radiation. Ionizing x-rays are produced by a device called a linear accelerator. Ionizing gamma rays can also be harnessed using nuclear material. These ionizing radiations are directed into a patient's body to treat both benign and malignant highly proliferating cells or undesired tissues. The success of such a treatment is highly dependent on the distribution of the radiation within the patient. Sub-optimal treatment delivery techniques can result in sub-optimal results, patient injury or even death. For this reason, much effort has been put forth by practitioners to create new equipment and algorithms to enhance the therapeutic ratio (benefit over negative side effects) of the radiotherapy treatment and increase the options available to patients Modern computational capabilities and modern equipment have enabled practitioners to create much more complex treatment plans that enhance the therapeutic ratio of the radiotherapy treatment. These advancements have simultaneously increased the chances of errors being undetected. For this reason, there is an increased need for new devices capable of verifying the planned dose distributions in a meaningful way.

In modern practice, it is common for practitioners to perform a verification measurement of the patient-specific radiotherapy plan on a patient surrogate. These surrogates are typically referred to as "radiotherapy phantoms" or just "phantoms". A radiotherapy phantom is a radiation attenuating medium such as water, PMMA (polymethyl methacrylate), metal, wood, gel, wax, plastic or any material having a radiation attenuation similar to water. The phantom will often contain or support a method for the detection and recording of the radiation dose distribution. A computer algorithm is used to predict the dose distribution within the phantom that would be produced if one were to deliver the patient plan to the phantom. During such a measurement a practitioner may place the phantom into a treatment room aligned in a known geometry within the treatment machine. Once the phantom is in place, the radiotherapy treatment plan is delivered. The measured dose is then compared to that which was predicted by the computer algorithm. If the result is within the acceptable criteria outlined by the institution, then the plan will proceed. If it does not meet criteria, the plan can be changed based on the results.

Recently, there has been increased interest and utilization of mono-isocentric delivery techniques. A mono-isocentric technique is one where a single plan with a single isocenter location is used to treat multiple treatment locations within the patient simultaneously. This trend is particularly relevant to stereotactic radiosurgery within the cranium. Utilization of this approach is likely to increase for the foreseeable future due to the desire to spare normal brain tissue as much as possible. The treatment targets may or may not lie directly on the central axis of the beam but in the case of multiple lesions (>2) they generally do not intersect with the isocenter. These "off-axis" fields cannot be easily or quickly measured using current phantom methods needs.

One significant difficulty in verification of mono-isocentric multiple lesion plans arises when a lesion does not lie directly on the isocenter. Many phantoms allow for the placement of measurement detectors in only very specific locations within the phantom body. This significantly limits the variety of tests that may be done.

Currently a multitude of phantoms exist on the market. The most commonly used are commercially available rectangular or cylindrically shaped phantoms. These geometries very poorly approximate the intended target (i.e. a head). Therefore, the interpretation and actual conclusions on the appropriate accuracy of the treatment plan are not truly evaluated. Further issues arise with these phantoms when electronic devices, like diode arrays, are used as the primary detection medium. Because their response is anisotropic and difficult to predict they must be irradiated from a certain direction or corrections must be applied to obtain the correct measurement. In the case of certain phantoms, like those with cylindrical geometry, all the planned therapy beams cannot be delivered as they will be delivered to the patient (i.e. with table "kicks"). This results in an approximate verification of the treatment plan where all possible parameters are not satisfactorily tested. Further, the final error analysis becomes difficult to interpret and little can be done to understand the source of error, if errors are detected.

SUMMARY OF THE INVENTION

According to one embodiment of the invention there is provided a spherical phantom for use with a source of radiation to receive a radiation dose distribution along a selected plane, comprising: a spherical body comprising two hemispheres detachably connected together and comprising a solid homogenous material including a hollow compartment with a defined volumetric shape; and a cartridge comprising a number of parallel planar plates each configured to accommodate a planar radiation detecting medium and fitting together to form a shape corresponding to the defined volumetric shape of the hollow compartment, wherein the cartridge fits form fittingly in the hollow compartment when the two hemispheres are connected together.

According to another aspect of the invention, there is provided a spherical phantom apparatus including the spherical phantom described above, and further comprising a stand to mount the spherical phantom for free rotation, respectively, about orthogonal axes crossing at the center of the sphere, wherein the spherical phantom is freely rotatable to place the planar radiation detecting medium accommodated by a selected one of the parallel plates in the selected plane containing the dose distribution generated by the source of radiation.

According to yet another aspect of the invention, there is provided a system comprising the spherical phantom apparatus described above and a computer processor for calculating a location of the radiation detecting medium within the cartridge and rotations of the spherical body about the equator and a meridian within the stand to place the radiation detecting medium in a plane containing up to three user chosen points of interest within the spherical body.

The above and other embodiments, aspects, details and advantages of the invention will become apparent from the following description taken in conjunction with the accompanying drawings.

DETAILED DESCRIPTION OF THE INVENTION

Figure 1:
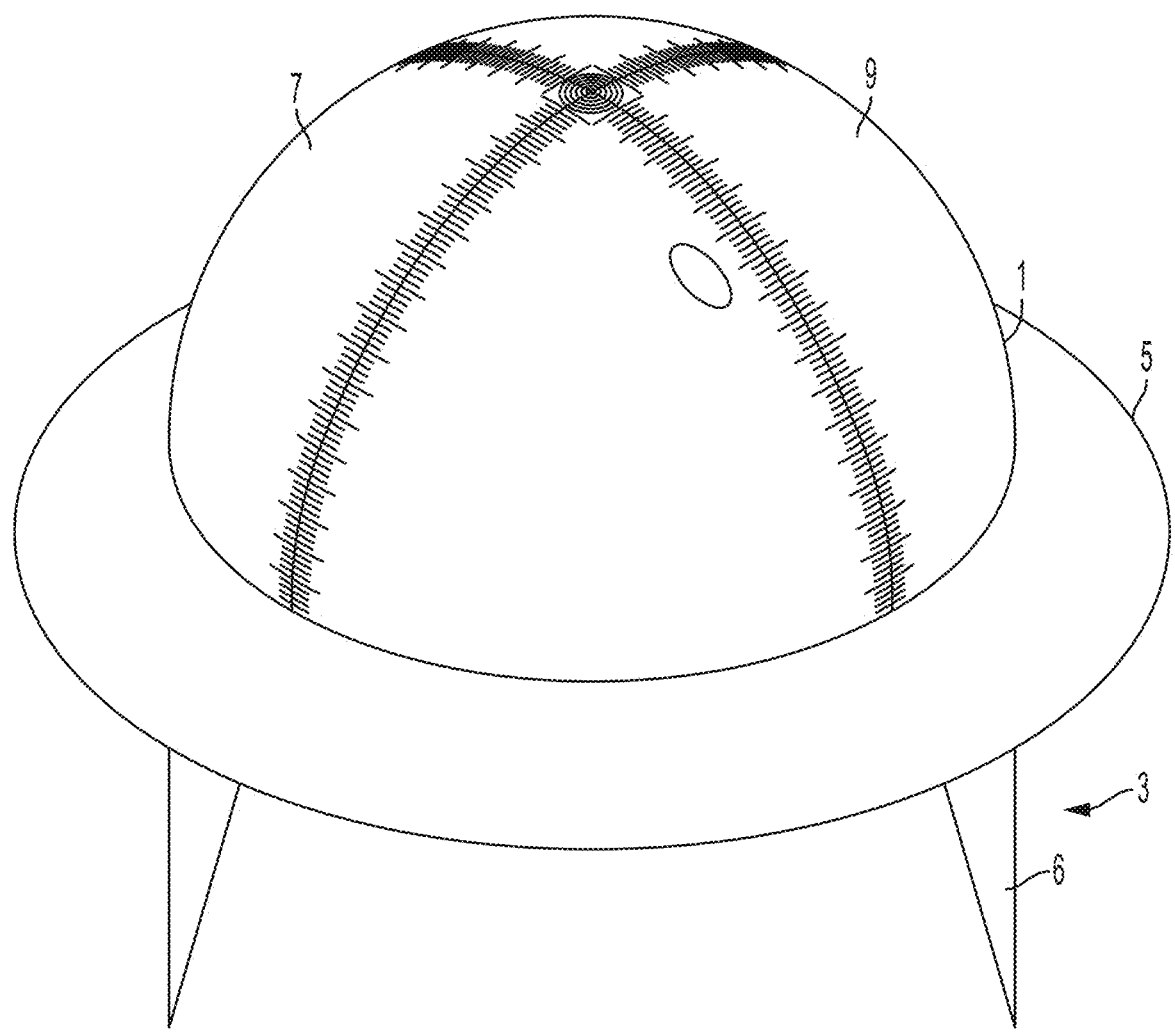
FIG. 1 is a perspective schematic showing a spherical radiotherapy phantom in a stand according to one embodiment of the invention.
Figure 2:
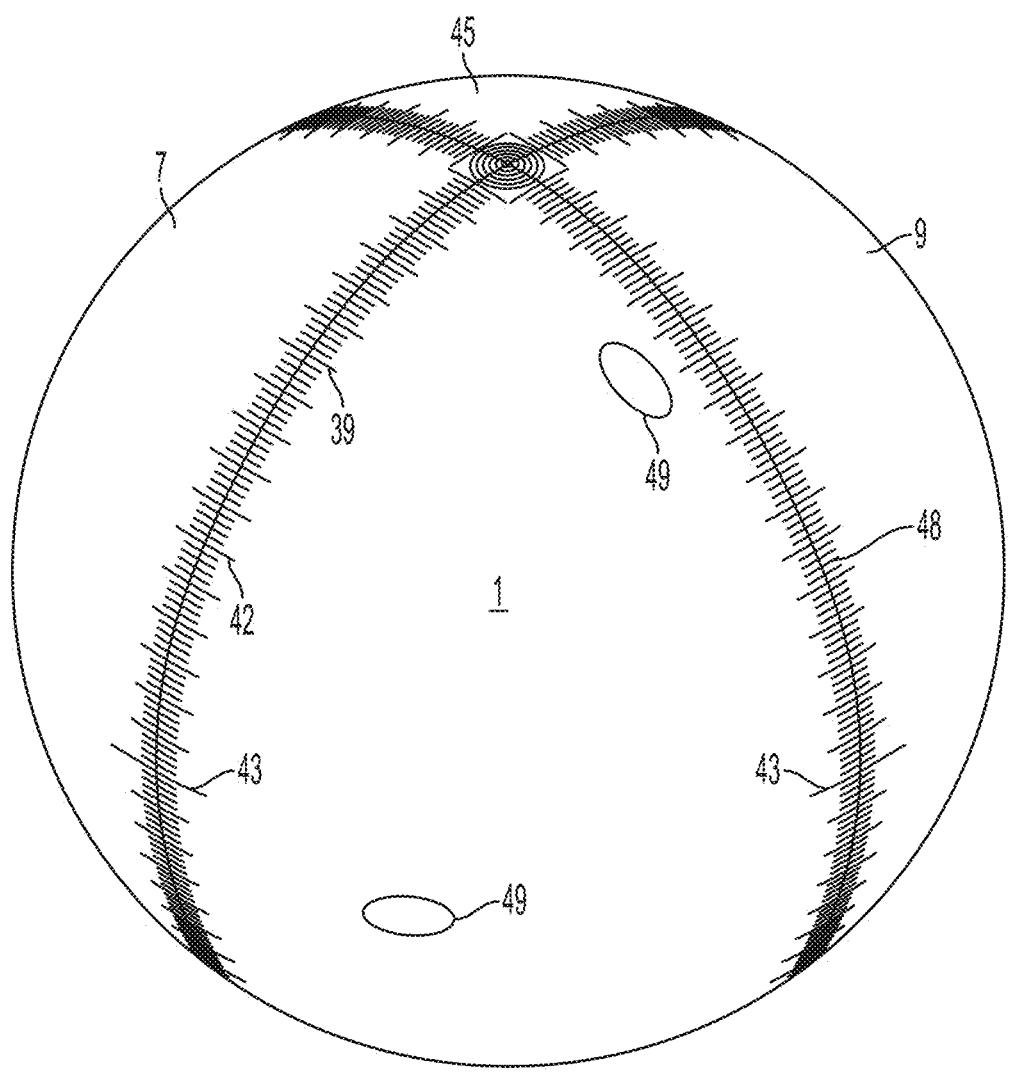
FIG. 2 is a perspective view of the spherical radiotherapy phantom shown in FIG. 1.

Referring to the FIGS. 1 and 2, there is shown a graphical depiction of a spherical radiotherapy phantom comprising a spherical body 1 according to the invention mounted in a simplified tripod stand 3 having a ring 5 supported by legs 6 in which the spherical body 1 is mounted for free rotation in any direction. The spherical body comprises multiple parts that are connected together to form a nearly homogeneous solid sphere as shown in FIG. 2. The spherical body comprises two hemispheres 7, 9, that are composed of a homogeneous material and designed such that when they are assembled they will define the spherical body. The spherical radiotherapy phantom also comprises a cartridge 13 as shown in FIG. 3 that fits within a hollow compartment inside the spherical body 1 as described below.

Figure 4:
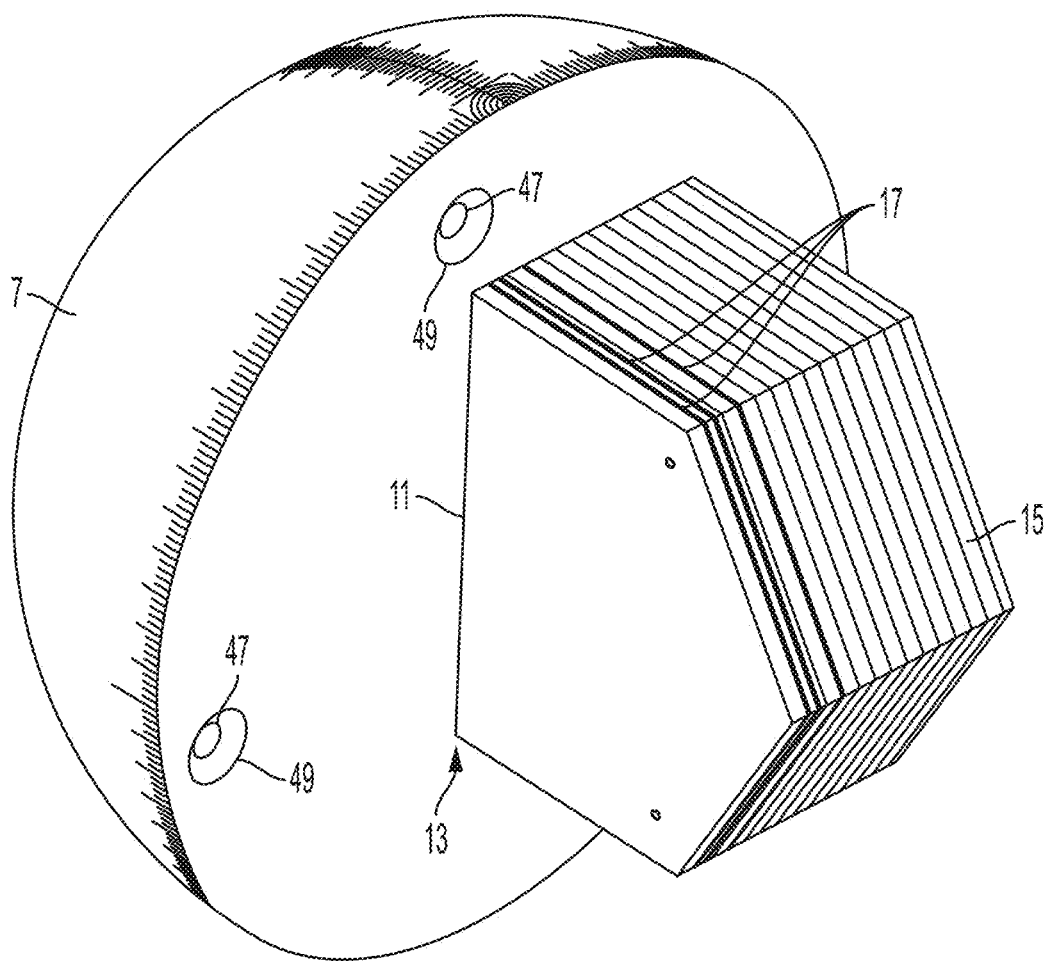
FIG. 4 is a perspective view of a spherical radiotherapy phantom with one hemisphere removed and with half the hexagonal cartridge buried in a partial compartment of the illustrated hemisphere and showing the other half of the cartridge that would fit in the partial compartment of the removed hemisphere, according to an embodiment of the invention.
Figure 5:
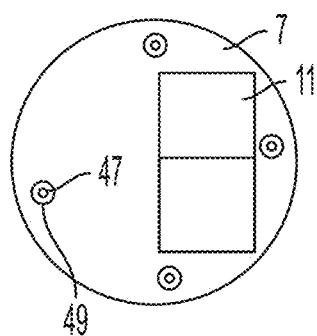
FIG. 5 is an end view of one hemisphere showing a portion of a hexagonal compartment in the hemisphere together with holes and connecting bolts of a latch system for connecting two hemispheres together according to an embodiment of the invention.

The two hemispheres are composed of solid material (e.g. polymethyl methacrylate) and are mirror images of each other. One such hemisphere 7 is depicted in FIGS. 4 and 5. FIG. 4 shows hemisphere 7, with hemisphere 9 of FIG. 2 being removed for ease of illustration. In FIG. 4, the non-illustrated hemisphere 9 is a mirror image of hemisphere 7. Below the equatorial plane, the part is solid and homogeneous in composition. Above the equatorial plane, a portion of material is removed to form a partial compartment 11 as shown in FIG. 5. When the two hemispheres are assembled, a full compartment is formed to house the entire cartridge 13. This compartment can have a variety of shapes including any polygon, cylinder or sphere. In the current embodiment, a half hexagonal shape has been removed from each hemisphere so that when the two hemispheres are brought together the resultant compartment is a hexagonal volume with a height of for example 70 mm. The use of a polygonal chamber, for example hexagonal, allows the user of the device to insert a cartridge to a known geometry within the sphere without worry of rotation of the interior cartridge, i.e. the cartridge is indexed within the sphere.

The compartment formed of two partial compartments 11 that are mirror images of one another will allow the insertion of the cartridge 13. The cartridge 13 comprises a set of parallel, planar plates 15, also referred to herein as insert plates, which when these insert plates are assembled, define the cartridge 13. The cartridge is made of material of similar composition to that of the spherical body 1. The spherical body and the cartridge each may comprise a material having a radiation attenuation comparable to water, such as PMMA, metal, wood, gel, wax, or Solid Water®, or any other material having a radiation attenuation equivalent to water. Solid Solid Water® is a trademark for an epoxy resin-based product having the required radiation attenuation equivalent to water. See for example, C. Constantinou, F. H. Attix and B. R. Paliwal, "A solid water phantom material for radiotherapy x-ray and γ-ray beam calibrations," Med. Phys., vol. 9, no. 3, pp. 436-441, 1982 and D. R. White, R. J. Martin and R. Darlison, "Epoxy resin based tissue substitutes," BJR, vol. 50, pp. 814-821, 1977.

Figure 3:
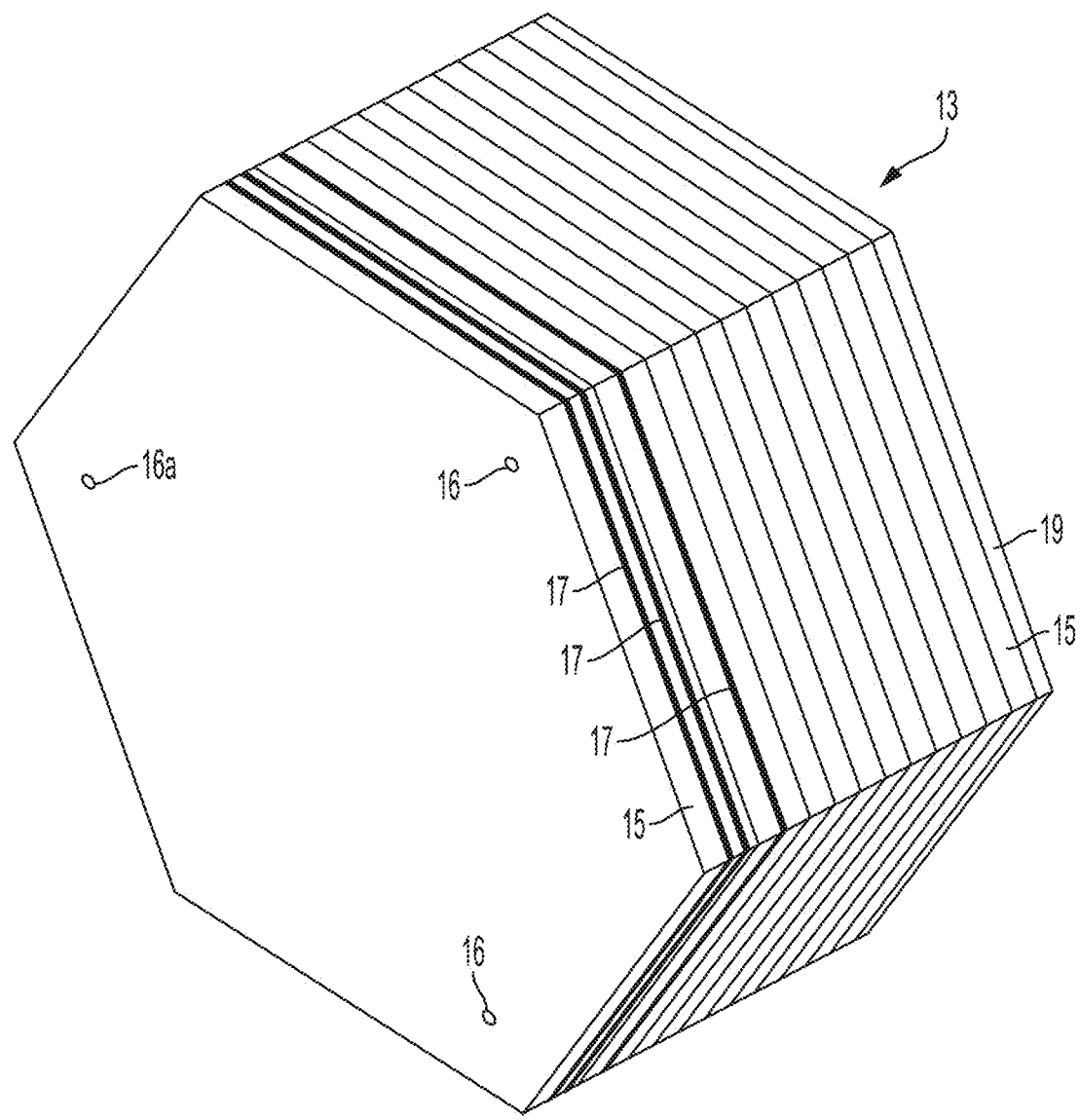
FIG. 3 is a bottom-side perspective view of a cartridge for use inside the spherical phantom of FIG. 2.
Figure 6:
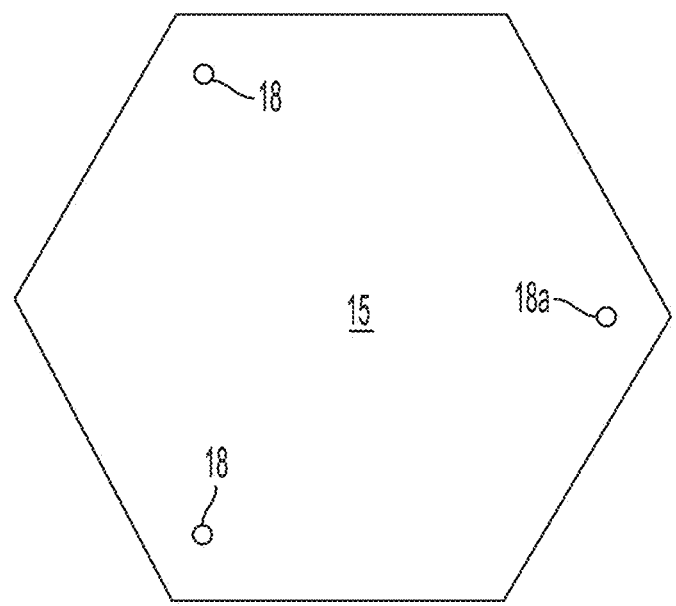
FIG. 6 is a top view of one of the interchangeable hexagonal insert plates in the cartridge of FIG. 3 showing aligning pins that fit in the recesses another plate thereabove in the cartridge.
Figure 7:
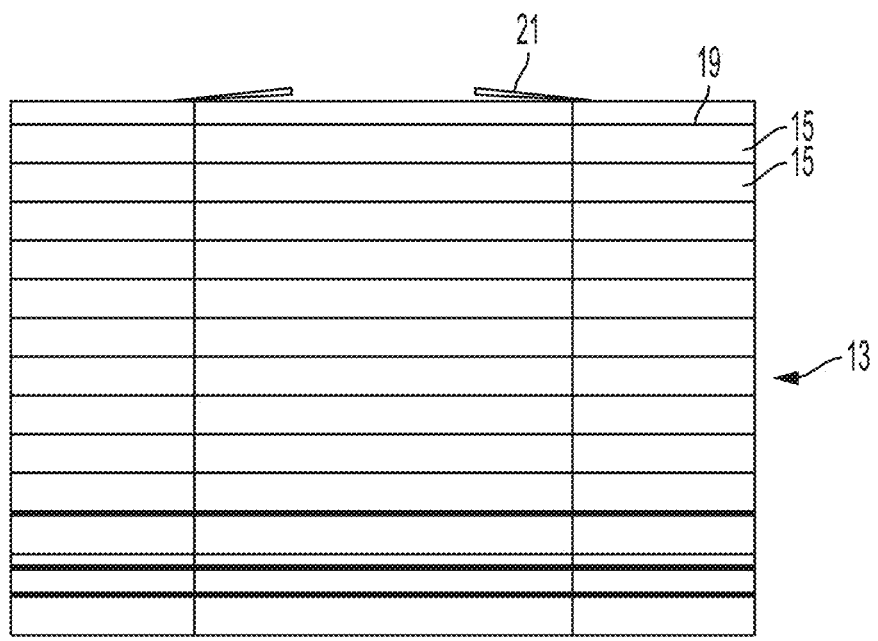
FIG. 7 is a side elevation of the stack of insert plates shown in FIG. 3.

As shown in FIG. 3, insert plates 15 may have one side containing spaced apart cylindrical recesses 16 having one diameter and another cylindrical recess 16a spaced from recesses 16 having a different, for example larger, diameter from that of recesses 16. FIG. 6 is a plan view of the opposite side of one of the insert plates 15 from that depicted in FIG. 3 showing similarly spaced apart pins 18 and 18a having diameters corresponding to the diameters of recesses 16 and 16a, respectively, for fitting into the recess so that the insert plates can be aligned and stacked one on top of the other to form the cartridge 13. FIG. 7 shows a side elevation of the cartridge 13 with the insert plates 15 stacked on top of one another and fixed in position via recess the recesses 16, 16a and pins 18 and 18a. The cartridge 13 will fully fill the compartment formed of the two partial compartments 11.

Figure 8:
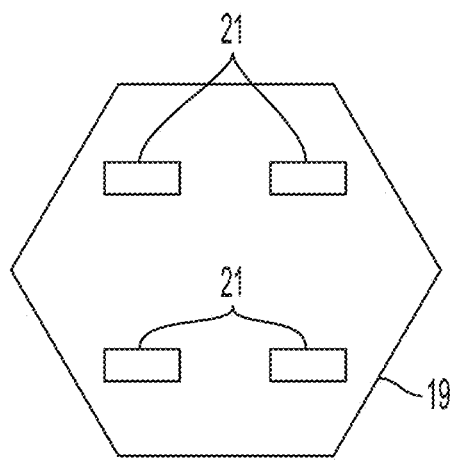
FIG. 8 is a top view of the top plate shown in FIG. 7.

In one embodiment, the cartridge itself may be made plates of different thicknesses, for example, the cartridge may comprise a stack of twelve 5 mm plates, one 3 mm plate, one 2 mm plate, as well as three thin plastic film markers 17 as shown in FIGS. 3 and 4. Also, the cartridge 13 may include one specialized top plate 19 (see FIGS. 7 and 8). The location of all plates and markers within the stack are interchangeable, with the exception of the top plate that must remain in the top position. As shown in FIGS. 7 and 8, the top plate 19 of cartridge 13 may include four protrusions 21, two protrusions will be located in each hemisphere. These protrusions are compressed when the stack is put into each partial compartment 11 of the spherical body 1. This allows the sphere to be rotated through any angle with the cartridge fixed tightly into its place within the compartment 11 of the spherical body. The interchangeability of the plates allows the user more flexibility and higher resolution by the placement location of the x-ray measurement medium (e.g. film).

The cartridge 13 will allow the insertion of an x-ray measurement medium in place of one or more of the markers 17, for example x-ray film, to one or more known locations within the cartridge. The x-ray measurement medium could also be an electronic medium which senses the radiation to create image data. The cartridge 13 will have a system to allow for the accurate placement of the radiation detecting medium to intersect with an arbitrary but pre-defined plane within three-dimensional space via predefined translations and rotations of the spherical body. The radiation detecting medium may have essentially the same peripheral dimensions as the insert plates 15 and have holes corresponding the locations of pins 18 and 18a on the insert plates 15 to be placed in registration with the insert plates.

Figure 9:
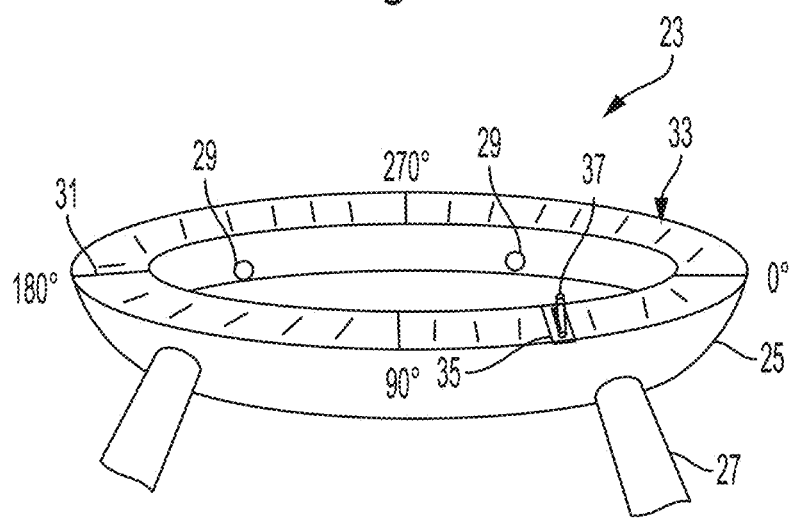
FIG. 9 is a perspective view of a schematic showing a stand for mounting the spherical radiotherapy phantom according to an embodiment of the invention.

FIG. 9 shows an embodiment of a stand 23 that may be used to rotatably support the spherical body 1. Ideally this stand will have low x-ray attenuation, for example comparable to air, and not produce CT artifacts. The stand 23 may comprise a light plastic tripod with a circular ring 25 of radius less than the radius of the spherical body, supported by legs 27. The stand may contain a plurality of free rotatable ball bearings 29, made for example of nylon spaced apart around an interior of the ring to allow free rotation of the spherical body within the stand. The ring 25 may also contain one or more spaced apart plungers 31 configured to allow the user to lock the spherical body 1 into a desired position within the stand according to set up instructions as discussed below, to restrict further rotation. The ring 25 may additionally contain on its upper surface angular measurement markings 33. The ring 25 may also be provided with a clear slider 35 that can be used to mark an angle along the ring 25. The ring may also be provided with an adjustable pointer or pin apparatus 37 that may assist in the rotation of the spherical body along its polar axis. A user may place the spherical body 1 into ring 25 of stand 23 and manually rotate the spherical body 1 as indicated by the setup instructions as discussed below.

An algorithm, as discussed below, will be used to instruct the user on proper placement of the measurement medium within the cartridge. This algorithm will further instruct the user to rotate and tilt the fully assembled spherical body, cartridge and film system so that measurement may be performed at a preselected but arbitrary plane within the body of the sphere.

As shown in FIG. 2, when assembled, the surface of spherical body may have markings 42 that represent angular coordinates at both the meridian 39 and the equator 41 of the spherical body. In one embodiment the markings are placed at 1-degree increments. The markings 42 may be longer every 5 degrees for easy identification. The 90-degree markings 43 may be extended in length compared to the 5-degree markings so that they can be easily identified. There may be a region 45 of markings on the surface of the sphere that consists of concentric circles as shown n FIG. 2. Using these rings, the user will easily identify the starting point of the angular coordinate system. Each concentric circle intersects with the equator and meridian such that a one-degree resolution is maintained on the equator and on the meridian. The spherical body will have a latch system comprised of bolts 47 threaded through holes 49 (see FIGS. 2, 4 and 5) that allows the spherical body to be separated into two hemispheres. In this embodiment four bolts are used which may be made of nylon or acrylic. It will be apparent to those skilled in the art that many latch systems and graphical system setups that result in a spherical geometry can be used to accomplish the final goal of a system which is to orient a planar x-ray measurement medium to a pre-defined plane in space.

A typical work flow will now be described with reference to FIG. 10. To setup the workflow the user will typically take a CT scan of the spherical radiotherapy phantom (51) in its totally assembled form, without the radiation detection medium. This CT scan will act as a virtual model from which future calculations will be based. In typical practice a potential radiation therapy treatment plan will be created in the hospitals treatment planning system (52) and mapped to the CT scan of the phantom (53). The user will export the dose distribution within the sphere and indicate to the sphere software system three points of interest within the dose distribution (54). These points may, for instance, represent the center of three dose clouds which surround three brain lesions. Importantly, these three dose points do not have to be on a plane that intersects with the origin of the sphere. Also, the process may be repeated multiple times if more lesions are present, for example 10 lesions, and the points may be chosen as the user sees fit. When the points of interest are chosen, the user will input the points of interest into a software (see below) to get a test setup geometry and to extract the dose distribution within the plane defined by those three points. The software program will then output setup instructions for the spherical phantom which will include the setup geometry for the sphere (55).

These setup instructions will instruct the user to place a radiation detecting medium, for example x-ray film, in an indicated position within the cartridge and to close the sphere around the loaded cartridge (56). Although, theoretically, a film may be placed on each plate 15, in the illustrated embodiment of FIGS. 3 and 4, 3 films may be used to replace the 3 depicted film markers 17. The user will then be instructed to reassemble the sphere with the film in place and to place the spherical phantom in the reference starting position (57). The user will be instructed to rotate the sphere along the equator to a designated angle Θ, for example 45 degrees, as indicated by room lasers, then tilt the sphere a designated angle Φ, for example 120 degrees, along the meridian markings (58). When the sphere has been correctly positioned, the user will be instructed to deliver the treatment plan as indicated by the treatment planning system. The film will be scanned according to a department's protocol and compared to the theoretical dose distribution indicated by the treatment planning system (59).

Figure 10:
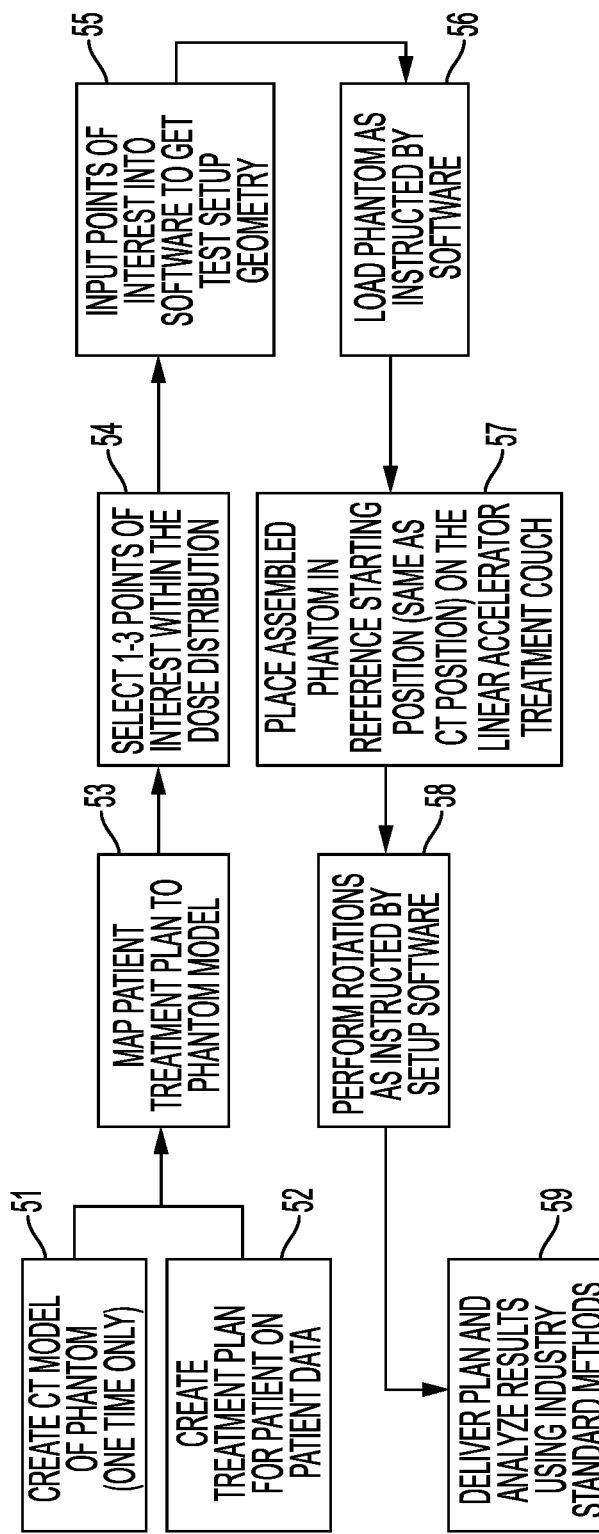
FIG. 10 is a work flow diagram for employing the spherical phantom according to the invention.

With reference to the stand illustrated in FIG. 9, an exemplary method of setup instruction according to FIG. 10 described above may be:
  Get output from software and load film as instructed (56);
  Place phantom in reference position (57);
  Move slider 35 in FIG. 9 to the target angle Θ and lock slider (58);
  Extend pin to align to equatorial plane (58);
  While keeping meridian line aligned with the pin 37 in FIG. 9, tilt the phantom until the tip of the pointer intersects with the desired Φ (58);
  Tighten locking plungers to secure the position of the spherical body 1 (S8);
  Deliver treatment plan to the sphere (59);
  Analyze (59).

Figure 11:
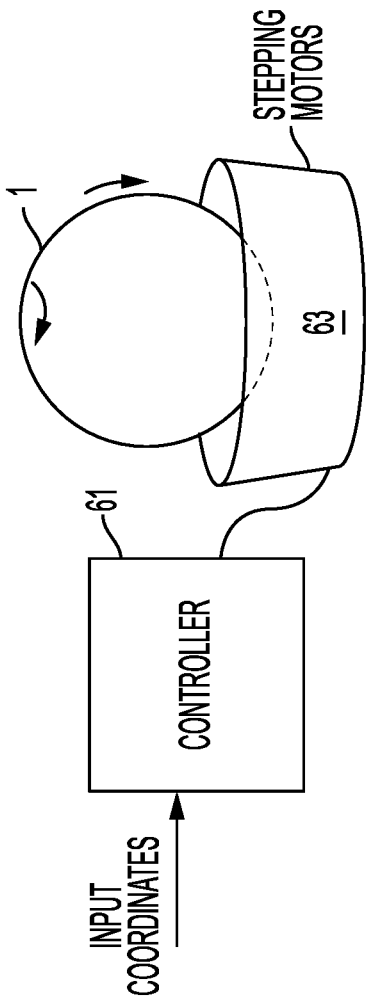
FIG. 11 is a partial block diagram and schematic of another embodiment of the invention showing the spherical radiotherapy phantom in a motorized stand for automatically moving the phantom to the desired meridian and equatorial angles.

According to another embodiment shown in FIG. 11, the setup may be automated by inputting the rotation coordinates into a controller 61 for controlling stepper motors 63 to rotate and tilt the spherical body 1 to the correct position.

A software program may be used to orient the sphere for a desired measurement. In use the user will have a CT model of the spherical phantom and will have an associated coordinate system attached to the sphere model in a starting position. The software will take as an input three user chosen coordinates P1=(x1, y1, z1), P2=(x2, y2, z2) and P3=(x3, y3, z3) that exist within the spherical model. All points should be chosen so that they exist within the body of the sphere, although this is not a restriction. Ideally the origin of the coordinate system is at the center of the spherical body. The software will then perform calculations to intersect a plane of the cartridge with all three coordinates for points P1, P2 and P3. An example of the calculation for arbitrary points P1, P2, and P3 follows:

1. Compute the unit vector normal n̂ to the chosen plane using the vector equation 1. In this equation the symbol "x" refers to the cross product and the symbol "•" refers to the dot product. The symbols "$r_x$" refer to the position vector of the points P1, P2, P3 in the coordinate system. So, the point P1 would have position vector $r_1$=<x1, y1, z1>.

$$\hat{n} = \frac{\vec{N}}{\|\vec{N}\|} = \frac{\overrightarrow{(r_2 - r_1)} \times \overrightarrow{(r_3 - r_1)}}{\pm\sqrt{\overrightarrow{\vec{N} \cdot \vec{N}}}}$$ (Equation 1)

2. The components of the unit normal vector will be some numbers (a, b, c). From this vector the desired rotations of the sphere using Equations 2 and 3 can be computed for the meridian and equatorial sphere rotations respectively:

$$\Phi = \cos^{-1} c$$ (Equation 2)

$$\theta = \sin^{-1}\left(\frac{b}{\sin \Phi}\right)$$ (Equation 3)

3. The software must now compute a plane that passes through any one of the points P1, P2 or P3 and is normal to the unit normal vector with components n=(a, b, c). Using vector calculus, the equation of one such plane (which passes through P1) has the equation given by Equation 4.

$$a(x-x1)+b(y-y1)+c(z-z1)=0$$ (Equation 4)

The software will construct a line along the unit normal vector as defined by the parametric equations 5a, 5b, and 5c as follows.

$$x(t)=at,$$ (Equation 5a)

$$y(t)=bt,$$ (Equation 5b)

$$z(t)=ct,$$ (Equation 5c)

The software will then find the point along this line that intersects with the previously computed plane by solving the equation for the location t. For this example, calculation of the solution is given by Equation 6.

$$t = \frac{-(a*x1 + b*y1 + c*z1)}{(a^2 + b^2 + c^2)}$$ (Equation 6)

In practice, the variable "t" will be discretized to the nearest possible location within the cartridge stack. The software will output the location of the detection medium (film) within the film cartridge and the rotations that should be performed prior to treatment test delivery. All parameters will have been discretized based on the physical dimensions of the spherical phantom (i.e. to the nearest degree of rotation and the nearest reachable location within the cartridge). Optionally the software may also contain a graphical interface to select the coordinates of interest (i.e. select lesions) and extract the desired treatment planning dose distribution along that plane from the DICOM (Digital Imaging and Communications in Medicine Standard) dose file.

Once the setup instructions are obtained from the software as described above, the user will take a piece of film and place it in the indicated position t within the cartridge. In the current embodiment, multiple films can be placed at once, but this will lower the cost efficiency. The user will then reassemble the sphere with the film in place, perform the setup tilts and shifts, and deliver the proposed treatment plan. The film will be scanned according to the department's protocol and compared to the theoretical dose distribution indicated by the treatment planning system.

It will be understood that the above description of the present invention is susceptible to various modifications, changes and adaptations, and that the same are intended to be comprehended within the meaning and range of equivalents of the appended claims.

What is claimed is:

1. A spherical radiotherapy phantom apparatus for use with a source of radiation to receive a radiation dose distribution along a selected plane, comprising:
   a spherical body comprising two hemispheres detachably connected together and comprising a solid homogenous material including a hollow compartment;
   a cartridge comprising a number of parallel planar plates each configured to accommodate a planar radiation detecting medium, wherein the cartridge is disposed in the hollow compartment when the two hemispheres are connected together; and
   a stand having a single mounting configuration to mount the spherical body for free rotation about any axis in three dimensional space passing through the center of the spherical body, wherein the spherical body is freely rotatable to place the planar radiation detecting medium accommodated by a selected one of the parallel plates in the selected plane containing the dose distribution generated by the source of radiation.

2. The spherical radiotherapy phantom apparatus according to claim 1, wherein the two hemispheres have symmetrically arranged interior hollow spaces that are mirror images of each other such that the hollow compartment is formed when the two hemispheres are attached together.

3. The spherical radiotherapy phantom apparatus according to claim 1, wherein the spherical body and the cartridge each comprise a material having a radiation attenuation comparable to water.

4. The spherical radiotherapy phantom apparatus according to claim 1, wherein the spherical body and the cartridge each comprise a material selected from a group including polymethyl methacrylate, metal, wood, gel, plastic, or Solid Water®.

5. The spherical radiotherapy phantom apparatus according to claim 1, wherein the radiation detection medium comprises x-ray film.

6. The spherical radiotherapy phantom apparatus according to claim 1, wherein the planar plates in the cartridge have different thicknesses.

7. The spherical radiotherapy phantom apparatus according to claim 6, wherein the cartridge includes plates having a thickness of 5 mm, 3 mm and 2 mm.

8. The spherical radiotherapy phantom apparatus according to claim 6, wherein the planar plates of different thickness are interchangeable to adjust the location of the radiation detecting medium within the sphere.

9. The spherical radiotherapy phantom apparatus of claim 1, further comprising one or more radiation detecting medium place holders each located between two planar plates of the cartridge.

10. The spherical radiotherapy phantom apparatus according to claim 1, wherein the cartridge includes an end plate including at least one flexible protruding region that is compressible into a plane of the end plate when the cartridge is placed into the hollow compartment of the spherical body.

11. The spherical radiotherapy phantom apparatus according to claim 1, wherein the planar plates include an arrangement of cylindrical openings on one side and a corresponding arrangement of pins on an opposite side having radii corresponding to the radii of the cylindrical openings to connect and align the plates one above the other to form the cartridge.

12. The spherical radiotherapy phantom apparatus according to claim 1, wherein the spherical body includes a latch system that allows the two hemispheres to be releasably connected together, wherein the two hemispheres are separable to allow loading of the cartridge into the hollow compartment.

13. The spherical radiotherapy phantom apparatus according to claim 1, wherein the stand includes at least one plunger arranged to lock the spherical body into the desired position.

14. The spherical radiotherapy phantom apparatus according to claim 1, wherein the stand has a radiation attenuation comparable to air.

15. The spherical phantom apparatus according to claim 1, wherein the stand includes a plurality of ball bearings arranged on an inner surface of the circular ring to facilitate free rotation of the spherical body on the ring.

16. The spherical phantom apparatus according to claim 1, wherein the circular ring has an upper surface including angular measurement markings.

17. The spherical phantom apparatus according to claim 16, wherein the stand includes a clear slider slidable on the circular ring and configured to mark a desired angular measurement marking along the ring.

18. A system comprising the spherical radiotherapy phantom apparatus of claim 1, and a computer processor for calculating a location of the radiation detecting medium within the cartridge and rotations of the spherical body within the stand along an equator and along a meridian of the spherical body to place the radiation detecting medium in a plane containing up to three user chosen points of interest within the spherical body.

19. The spherical radiotherapy phantom apparatus according to claim 1, wherein the hollow compartment has a defined volumetric shape, and the parallel planar plates fit together to form a shape corresponding to the defined volumetric shape of the hollow compartment, wherein the cartridge is disposed form fittingly in the hollow compartment when the two hemispheres are connected together.

20. A spherical radiotherapy phantom for use with a source of radiation to receive a radiation dose distribution along a selected plane, comprising:
    a spherical body comprising two hemispheres detachably connected together and comprising a solid homogenous material including a hollow compartment; and
    a cartridge comprising a number of parallel planar plates each configured to accommodate a planar radiation detecting medium, wherein the cartridge is disposed in the hollow compartment when the two hemispheres are connected together;
    wherein the spherical body has a surface with an equator circle in an imaginary plane through the center of the spherical body and a meridian circle intersecting the equator circle, wherein at least one of the equator circle and meridian circle have angular markings with respect to the center of the spherical body.

21. The spherical radiotherapy phantom according to claim 20, wherein an intersection of the equator circle with the meridian circle comprises a reference point, and further including a region containing concentric markings with the reference point being at the center of the concentric markings.

22. The spherical radiotherapy phantom according to claim 20, wherein the imaginary plane is between the two hemispheres.

* * * * *